(12) United States Patent
Zeng et al.

(10) Patent No.: US 12,227,781 B2
(45) Date of Patent: Feb. 18, 2025

(54) METHODS USING PHOTOTHERMAL NANOPARTICLES IN RAPID NUCLEIC ACID AMPLIFICATION AND PHOTOTHERMAL NANOPARTICLES

(71) Applicant: Promega Corporation, Madison, WI (US)

(72) Inventors: Zhiyang Zeng, San Luis Obispo, CA (US); Maria Perez Cardenas, San Luis Obispo, CA (US); Cesear Corona, Paso Robles, CA (US); Wenhui Zhou, San Luis Obispo, CA (US); Poncho Meisenheimer, Madison, WI (US); Doug Storts, Fitchburg, WI (US); Andrew Taft, Fitchburg, WI (US)

(73) Assignee: Promega Corporation, Fitchburg, WI (US)

( * ) Notice: Subject to any disclaimer, the term of this patent is extended or adjusted under 35 U.S.C. 154(b) by 684 days.

(21) Appl. No.: 16/880,917

(22) Filed: May 21, 2020

(65) Prior Publication Data
US 2020/0370083 A1 Nov. 26, 2020

Related U.S. Application Data

(60) Provisional application No. 62/851,403, filed on May 22, 2019.

(51) Int. Cl.
| | |
|---|---|
| C12P 19/34 | (2006.01) |
| C12N 15/10 | (2006.01) |
| C12Q 1/686 | (2018.01) |
| B82Y 5/00 | (2011.01) |

(52) U.S. Cl.
CPC .......... *C12P 19/34* (2013.01); *C12N 15/1006* (2013.01); *C12Q 1/686* (2013.01); *B82Y 5/00* (2013.01); *C12Q 2523/313* (2013.01); *C12Q 2563/155* (2013.01)

(58) Field of Classification Search
CPC ..... C12P 19/34; C12N 15/1006; C12Q 1/686; C12Q 2523/313; C12Q 2563/155; C12Q 2565/628; B82Y 5/00
See application file for complete search history.

(56) References Cited

U.S. PATENT DOCUMENTS

| | | | |
|---|---|---|---|
| 2012/0046593 A1 | 2/2012 | Oraevsky et al. | |
| 2014/0170664 A1 | 6/2014 | Roche et al. | |
| 2016/0076086 A1 | 3/2016 | Vo-Dinh et al. | |
| 2017/0000547 A1 | 1/2017 | Harris et al. | |
| 2018/0080064 A1 | 3/2018 | Lee et al. | |
| 2018/0193910 A1 | 7/2018 | Kircher et al. | |

FOREIGN PATENT DOCUMENTS

| | | | |
|---|---|---|---|
| WO | 2016115542 A1 | 7/2016 | |
| WO | WO-2016200525 A1 * | 12/2016 | ............ B22F 1/0018 |

OTHER PUBLICATIONS

Lee et al, Plasmonic Photothermal Gold Bipyramid Nanoreactors for Ultrafast Real-Time Bioassays, 2017, J. Am. Chem. Soc. 2017, 139, 8054-8057, Published May 1, 2017. (Year: 2017).*
Lee et al, Plasmonic Photothermal Gold Bipyramid Nanoreactors for Ultrafast Real-Time Bioassays, 2017, J. Am. Chem. Soc. 2017, 139, 8054-8057, supporting information s1-s16. (Year: 2017).*
Wang et al , Understanding the photothermal effect of gold nanostars and nanorods for biomedical applications, RSC Adv., 2014, 4, 30375-30383. (Year: 2014).*
Shamraiz, et al , Gold nanotubes and nanorings: promising candidates for multidisciplinary fields, International Materials Reviews, 2018, pp. 1-35. (Year: 2018).*
Kim et al, Plasmonic Photothermal Nanoparticles for Biomedical Applications, 2019, Adv.Sci., 6, pp. 1-23 (Year: 2019).*
Roche et al. "Demonstration of a Plasmonic Thermocycler for the Amplification of Human Androgen Receptor DNA," Analyst, Jul. 17, 2012 (Jul. 17, 2012), vol. 137, pp. 4475-4481, entire document.
Yukina Takahashi et al., Photoenergy Conversion Systems by Utilizing Localized Surface Plasmon Resonance Based on Metal Nanostructures, Journal of the Japan Society of Colour Material, vol. 90, No. 12, pp. 426-430 (2017), (English Abstract).
Hiroaki Agawa et al., Photothermal Conversion Using Localized Surface Plasmon Resonance, Journal of the Japan Society of Colour Material, vol. 90, No. 12, pp. 414-419 (2017), (English Abstract).

* cited by examiner

*Primary Examiner* — Narayan K Bhat
(74) *Attorney, Agent, or Firm* — Dicke, Billig & Czaja, PLLC

(57) ABSTRACT

Methods using photothermal nanoparticles in rapid nucleic acid amplification and photothermal nanoparticles include forming a reaction mixture comprising a nucleic acid template, a polymerase enzyme, and a heating media. The heating media comprises a plurality of photothermal nanoparticles suspended in a solution, fabricated on a microchip, or on a surface of a well in a multi-well plate. The photothermal nanoparticles are nanoparticles having a particular geometric shape and comprise a single component or a multi-component. The plurality of photothermal nanoparticles are further categorized by surface plasmon resonance with a resonance wavelength in a particular range to convert energy absorbed from a light source to sufficiently heat a volume of a composition for the transcription of the new nucleic acid strand. The particular geometric shape of the photothermal nanoparticles is selected from the group consisting of: polyhedral, spheroid, torus, and hollow shapes.

13 Claims, 16 Drawing Sheets

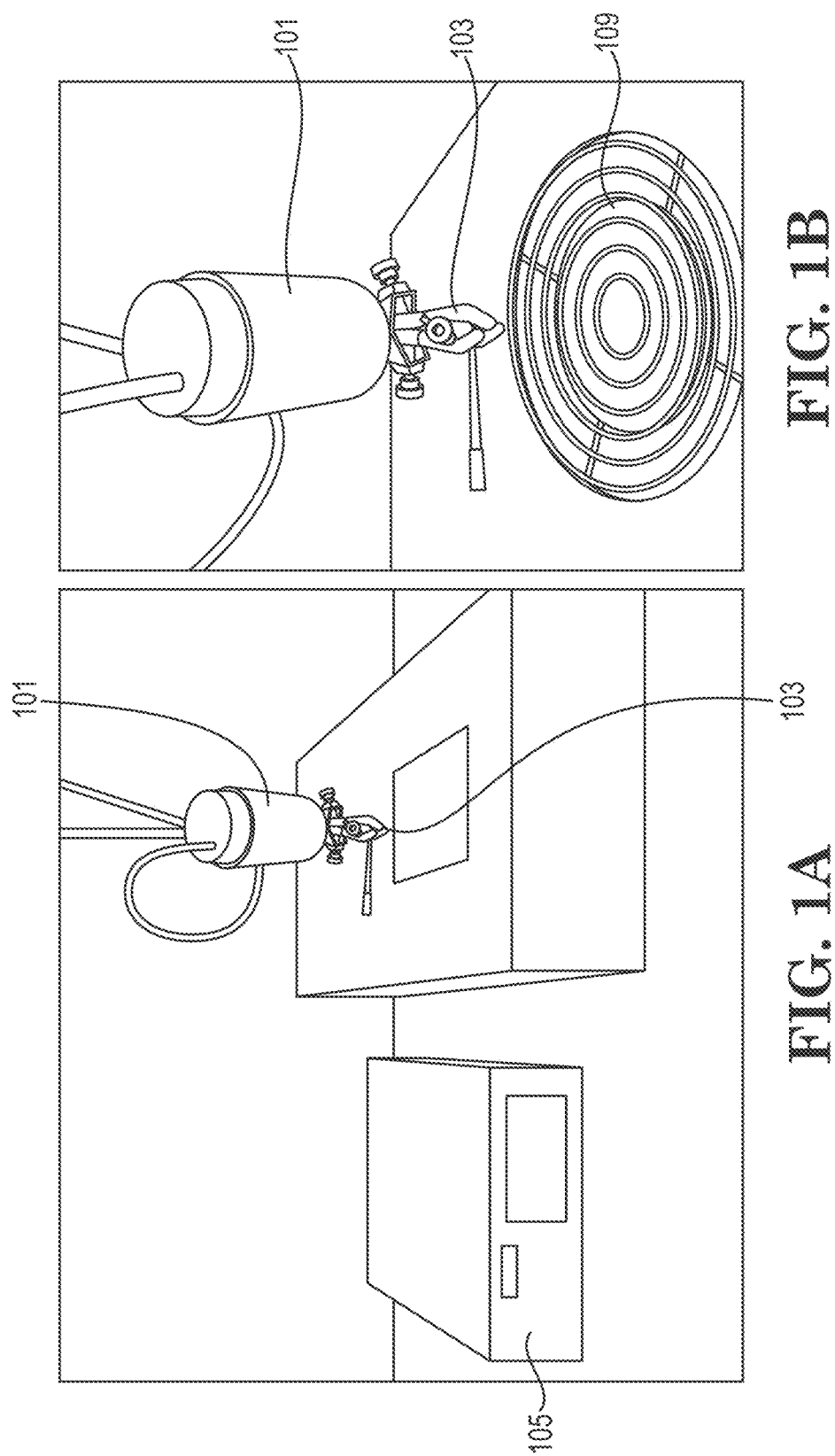

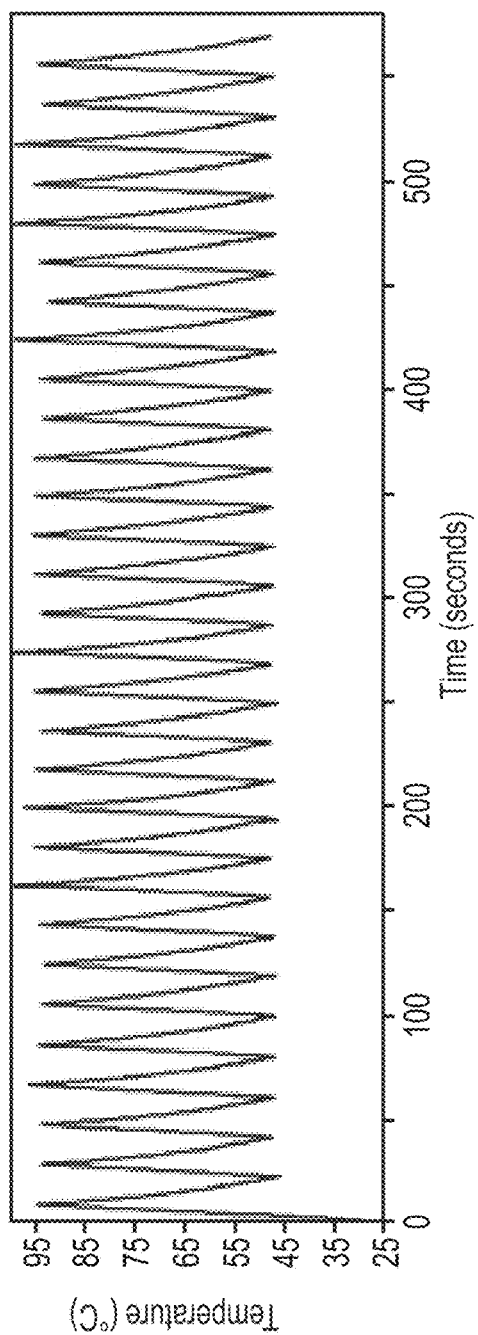
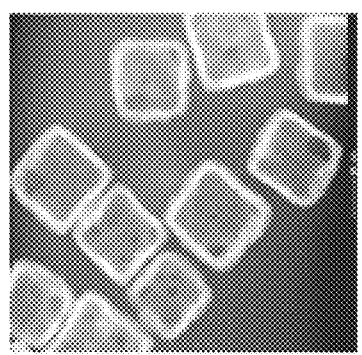
FIG. 3E
FIG. 3F

METHODS USING PHOTOTHERMAL NANOPARTICLES IN RAPID NUCLEIC ACID AMPLIFICATION AND PHOTOTHERMAL NANOPARTICLES

INCORPORATION BY REFERENCE

This application claims the benefit of, and incorporates herein in its entirety, U.S. Provisional Patent Application Ser. No. 62/851,403 filed on May 22, 2019, and entitled "METHODS USING PHOTOTHERMAL NANOPARTICLES IN RAPID NUCLEIC ACID AMPLIFICATION AND PHOTOTHERMAL NANOPARTICLES."

OVERVIEW

Described herein are methods of using nanoparticles as a heating media in a polymerase chain reaction (PCR) mixture, which can be heated at a rate up to 75 degrees Celsius/second to complete amplification thermal cycles in less than 15 minutes. A typical PCR can take up to few hours to complete depending on the quality and concentration of the target nucleic acid. This slow cycle time cannot meet the demand of many current genetic amplification applications. Therefore, various aspects of embodiments herein are directed to rapid nucleic acid amplification using nanoparticles as a heating media to speed up cycling in PCR. Further described herein are plasmonic nanoparticles that absorb energy from light (e.g., from a light emitting diode or laser) and convert it to heat, thereby becoming photothermal nanoparticles. The photothermal nanoparticles described in the present invention have a variety of geometric shapes that have been derived to meet extinction peak wavelengths ranging from about 300 nanometers (nm) to 1500 nm. These photothermal nanoparticles can be used as a heat media in PCR mixtures to provide faster heat cycles, and thereby faster PCR cycle times (e.g., less than 15 minutes (min) for 30 cycles or more) that will dramatically increase the workflow efficiency in PCR-based technologies.

BRIEF DESCRIPTION OF FIGURES

Various example embodiments may be more completely understood in consideration of the following detailed description in connection with the accompanying drawings in which:

FIGS. 1A and 1B illustrate a diagram of a photothermal testing system to evaluate the nanoparticles photo-to-heat conversion for rapid nucleic acid amplification in accordance with the present disclosure;

FIG. 3E illustrates example photothermal cycles of gold nanostars coated with polyethylene glycol in accordance with the present disclosure;

FIG. 3F illustrates an example TEM image of gold nanostars in accordance with the present disclosure;

Figure 2A:
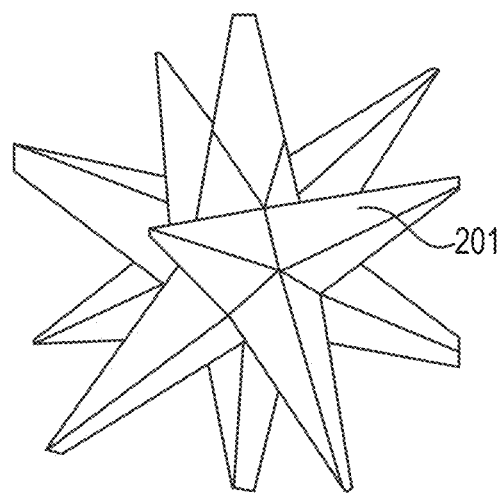
FIGS. 2A-2U illustrate example photothermal nanoparticles in accordance with the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems, and methods involving rapid nucleic acid amplification using nanoparticles. Nanoparticles having a particular geometric shape can be selected for their photothermal profile such that nucleic acid amplification can be rapidly performed. At a specific wavelength of light, collective oscillation of electrons on the nanoparticle surface cause a phenomenon called surface plasmon resonance. The particular wavelength of light where this occurs is dependent on the nanoparticle size, shape, and composition. For instance, nanoparticles having a particular geometry (e.g., shape and/or size) and/or having a particular composition and/or surface coating can be selected to have a maximum peak extinction wavelength ranging from 300 nm to 1500 nm enabling photon to heat conversion for polymerase chain reaction (PCR). In certain implementations, aspects of the present disclosure have been shown to be beneficial in the context of amplifying nucleic acids using PCR with plasmonic, photothermal nanoparticles used as a heating media to increase the heating cycle of the PCR reactions. While not necessarily so limited, various aspects may be appreciated through the following discussion of non-limiting examples which use exemplary contexts.

PCR is a method widely used in molecular biology to make many copies of a nucleic acid segment. Using PCR, a single copy (or more) of a nucleic acid sequence is exponentially amplified to generate thousands to millions or more copies of that particular nucleic acid segment. The vast majority of PCR methods rely on thermal cycling. Thermal cycling exposes reactants to repeated cycles of heating and cooling to permit different temperature-dependent reactions to occur.

A typical PCR reaction can take up to a few hours to complete depending on the quality and concentration of the target nucleic acid. This cycle time cannot meet the demand of many, current genetic amplification applications. Faster PCR cycle times (for example, less than 15 minutes (min) for 30 cycles) can increase the workflow efficiency in PCR-based technologies, and hence the downstream applications such as next generation sequencing (NGS). Consistent with various examples of the present disclosure, plasmonic photothermal nanoparticles are used as heating media to speed up the heating cycle of PCR.

A number of embodiments of the present disclosure are directed to plasmonic photothermal nanoparticles of a variety of different shapes and/or different shape combinations for use as a heating media for PCR-based reaction mixtures. These nanoparticles absorb energy from a light source such as lasers or light emitting diode (LEDs) with a wavelength of about 300 nm to 1500 nm and convert the light to heat and to heat a PCR mixture rapidly at a rate up to 75 degrees C./second. In some embodiments, the nanoparticles heat a PCR mixture rapidly at a rate of up to 40 degrees C./second. In some embodiments, the nanoparticles heat a PCR mixture rapidly at a rate of up to 20 degrees C./second. In some embodiments, the nanoparticles heat a PCR mixture rapidly at a rate of up to 10 degrees C./second. These nanoparticles are also stable under light irradiation and have high photo-to-thermal conversion efficiency. The photothermal nanoparticles described herein may be composed of metals or alloys with or without inorganic or organic surface coating. The nanoparticles may be composed of metals including, but not limited to, gold (Au), silver (Ag), platinum (Pt), palladium (Pd), iron (Fe), copper (Cu), aluminum (Al), zinc (Zn), and combinations thereof with or without an alloy.

The plasmonic photothermal nanoparticles described herein have a particular geometry and/or shape that is non-spherical and/or non-rod shaped. For instance, the nanoparticles can have a shape (e.g., geometry) including, but not limited to the following: nanostar, nanotriangle/prism, nanohexapod, hexagonal rings, nanocube, nanoring, nanocage, nanosquare plate, trisoctahedra, rhombicadodecadra, truncated ditetragonal prism, tetrahexahedra, octahedra, decahedra, icosahedra, nanobar, hexagonal plates, rice-like shapes, disk, and combinations thereof. The photothermal nanoparticles described in the present invention may also be coated with an organic or inorganic material(s) to prevent interference by PCR-based reaction components due to a bare particle surface and/or enhancement of the stability of the nanoparticle under irradiation and during storage. These coating materials include, but are not limited to, silica, synthetic polymers (such as polyvinylpyrrolidone(PVP), thiol terminated Polystyrene, polyacrylamide), oligo or polyethylene glycol, peptides, polysaccharides, non-polymeric coatings, etc. As an illustration, the photothermal nanoparticles may be coated with gold and/or coated with a gold-silver alloy. Such photothermal nanoparticles may have a particular geometry and a particular chemical coating sufficient to maintain stability under irradiation and to maintain a high photo-to-thermal conversion efficiency. To engage the photothermal property of the nanoparticles, the light source can be a laser or LED, with the requirement being that the input power is sufficient for rapid heating ramp at a rate up to 75 degrees C./s. The described geometries, shapes, and/or surface coatings of the nanoparticles can provide higher photo-to-thermal conversion efficiency as well as higher shape stability during irradiation, thereby preventing nanoparticle melting during irradiation by the light source.

Photothermal nanoparticles absorb energy from light, such as a light emitting diode (LED), and convert it to heat. In accordance with various embodiments of the present disclosure, a PCR mixture with nanoparticles can be heated at a rate up to 75 degrees Celsius (C) per second to complete 30 or more cycles in 15 min or less time by adjusting the concentration of photothermal nanoparticles. In some embodiments, the nanoparticles heat a PCR mixture at a rate of up to 40 degrees C./second. In some embodiments, the nanoparticles heat a PCR mixture rapidly at a rate of up to 20 degrees C./second. In some embodiments, the nanoparticles heat a PCR mixture rapidly at a rate of up to 10 degrees C./second. Additionally, these photothermal nanoparticles can be tuned to have a variety of peak wavelengths ranging from 300 nm to 1500 nm by adjusting the composition and shape of the nanoparticle. This also enables not only the end-point PCR-based applications, but also real-time PCR-based applications with fluorescent dyes present in the reaction mixture.

PCR is a temperature-mediated process that requires cycling between set temperatures. Single-strand nucleic acids are required for two primer sequences to bind upstream and downstream of the region to be amplified. To allow for amplification to occur, a first step is denaturation or separation of the two strands at around 94-98 degrees C. Primer annealing occurs around 45-55 degrees C. and allows the thermo-stable polymerase to bind to defined regions of double stranded deoxyribonucleic acid (DNA). A next stage is elongation of the double stranded copy where the temperature is raised to the optimum temperature (around 72 degrees C.) for the enzyme catalysis to proceed. Finally, temperature is returned to 94 degrees C. for denaturation to single-stranded DNA that allows the cycle to repeat. As may be appreciated to one of ordinary skill in the art, the PCR process can additionally include cooling steps.

Increasing the speed can increase the efficiency of PCR processes. The thermocycling of a PCR process can be dependent upon several factors, including the experimentalist's requirements. Additional time to complete PCR is a function of the time to reach the desired temperatures for the temperature-mediated processes (e.g., denaturation, primer annealing, and elongation/synthesis). Shortening ramp and cooling times results in more rapid transition and shorter cycling times.

PCR is carried out in a reaction volume. The reaction volume/mixture contains one nucleic acid to be amplified, which is termed "the original" or "sense" strand. In the reaction volume, the sense strand can be in a double-strand form with its complementary strand, which is termed "the complement" or "antisense" strand. If the sense and antisense strands are present as a double-strand DNA molecule, this double-strand DNA molecule is denatured in a first step of PCR, i.e., the double-strand DNA molecule is split into two single strands, e.g., the sense and antisense strands. In a first step of PCR, the two strands of a double-stranded molecule (e.g., DNA or RNA) are physically separated at a high temperature in a process called denaturation or melting. Denaturation occurs at a temperature, which is termed denaturing temperature. The reaction volume/mixture further contains at least two primers. "Primers" refer to or include short single-strand nucleic acid segments, which are also known as oligonucleotides, which are a complementary sequence to the target nucleic acid sequence. One of the primers is termed a forward primer while the other is termed a reverse primer. The forward primer is complementary to the 3'-end of the sense strand. The reverse primer is complementary to the 3'-end of the antisense strand.

In the second step of PCR, the temperature is lowered, and the primers hybridize/bind to their complementary sequences on the nucleic acid sequence. The two, now double-stranded, nucleic acid strands then become templates for an enzymatic reaction using a polymerase to transcribe a new nucleic acid strand from free nucleotides that are also found in the reaction volume/mixture. The forward primer hybridizes to a sequence in the sense strand while the reverse primer hybridizes to a sequence in the antisense strand. The hybridization of the primers with the complementary sequences of the sense strand or antisense strand is termed annealing. This second step takes place at a temperature termed the annealing temperature.

The reaction volume/mixture further contains a DNA polymerase. In a third step, the DNA polymerase synthesizes a copy of the complement starting from the forward primer and synthesizes a copy of the sense strand starting from the 5' end of the reverse primer. Throughout the synthesis, the copy of the antisense strand also hybridizes with the sense strand and the copy of the sense strand hybridizes with the antisense strand. This third step is termed elongation and is carried out at a temperature called the elongation temperature. After the elongation step, the first, second, and third steps are repeated until the desired extent of amplification is achieved, wherein multiple copies of the sense and antisense strands are made. As PCR progresses, the nucleic acid generated is itself used as a template for replication, setting in motion a chain reaction in which the original nucleic acid template is exponentially amplified.

PCR is commonly carried out in a volume of 10-200 microliters (µL) in small reaction tubes (e.g., 0.2-0.5 milliliter (mL) volumes) in a thermal cycler. The thermal cycler (also known as a Thermocycler, PCR Machine, or DNA Amplifier) is an apparatus used to amplify segments of DNA via the PCR process. Thermal cyclers are typically provided with a thermal block with holes where tubes holding the PCR reaction volumes/mixtures can be inserted. Heat is provided through solid state heaters or infrared lamps. The thermal cycler raises and lowers the temperature of the thermal block in discrete, preprogrammed steps. The thermal cycler heats and cools the reaction tubes to achieve the temperatures required at each step (e.g., cycle) of the reaction. Many modern thermal cyclers make use of the Peltier effect, which permits both heating and cooling of the block holding the PCR tubes by reversing the electric current. Thin-walled reaction tubes permit thermal conductivity to allow for rapid thermal equilibration. As the separate steps of the PCR can be carried out at different temperatures, it can be necessary to perform one or several heating steps, and where applicable, cooling steps during or between the steps of the PCR in which the reaction volume or parts thereof are cooled. In accordance with various embodiments of the present disclosure, the reaction volume/mixture further includes a heating media including photothermal nanoparticles that can locally and rapidly heat a reaction volume/mixture to target temperatures to expedite the PCR cycling time.

In a typical PCR, the denaturing temperature is chosen such that the single strands of the nucleic acid denature while not effecting, e.g., damaging, the polymerase. A typical denaturing temperature is about 95 degrees C. The optimal annealing temperature usually depends on the sequence and length of the primers. Typically, primers are designed for an annealing temperature between about 50 degrees C. and 65 degrees C. The optimal elongation temperature typically depends on the DNA polymerase used. For example, if using Taq DNA polymerase, an elongation temperature of about 72 degrees C. is commonly used. After elongation, the temperature is returned to 94 degrees C. for denaturation of the double-stranded DNA to single-stranded DNA. This cycling from denaturation-annealing-elongation is repeated a number of times, typically 20 to 40 cycles.

As discussed above, several components and reagents are commonly used in PCR. Among these components are, a nucleic acid template, such as a DNA template (e.g., double-stranded DNA) that contains the target sequence to be amplified, an enzyme that polymerizes new nucleic acid strands (e.g., a polymerase enzyme such as DNA polymerase, e.g., Taq DNA polymerase), two nucleic acid primers (oligonucleotides, e.g., single-stranded) that are complementary to the 3' (three prime) ends of each of the sense and antisense strands of the nucleic acid target, nucleoside triphosphates (NTPs) such as deoxyribonucleotide triphosphates (dNTPs) and ribonucleoside triphosphates (rNTPs), and a buffer solution providing a suitable chemical environment for amplification and optimum activity and stability of the polymerase. Specific buffer solutions often include bivalent cations, such as magnesium (Mg) or manganese (Mn) ions, and monovalent cations such as potassium (K) ions. Consistent with various examples of the present disclosure, the reaction mixture can further include a heating media including photothermal nanoparticles having a particular geometry that allow for rapid heating of the reaction mixture. The addition of a heating media provides a drastic reduction in the time needed for PCR cycling.

In various examples of the present disclosure, the method of nucleic acid amplification generally includes the steps of contacting the reaction volume/mixture containing a nucleic acid template with photothermal nanoparticles and irradiating the nanoparticles using an activation light source such that the reaction volume/mixture reaches a desired temperature. Accordingly, instead of using Peltier heaters or infrared lamps to transfer heat to the vessel containing the reaction mixture, the reaction of the present disclosure is heated to the desired temperature for the PCR using the photothermal nanoparticles to heat the reaction volume/mixture. In various examples, the whole reaction mixture, half the reaction mixture, less than half the reaction mixture, or a small amount of the reaction mixture around nanoparticles are irradiated.

In some examples of the present disclosure, the method includes forming a reaction mixture including a nucleic acid template, a polymerase enzyme, and photothermal nanoparticles either suspended in the solution or immobilized on a microchip or on the surface of a well of a substrate such as a multi-well plate. As described herein, the photothermal nanoparticles can be nanoparticles having a particular geometric shape and comprising a single component or multicomponents. The plurality of plasmonic photothermal nanoparticles can have a resonance wavelength in a particular range to convert energy absorbed from a light source to sufficiently heat a volume of the composition for the transcription of the new nucleic acid strand. For instance, the particular geometric shape can be selected from the group consisting of: polyhedral, spheroid, torus shapes, among other shapes.

As described more thoroughly herein, the particular geometric shape can include a polyhedral nanoparticle. The polyhedral nanoparticle can be non-symmetrical. For instance, the nanoparticle can have a plurality of faces, where at least two of the plurality of faces have a different shape or size as compared to a remainder of the plurality of faces. As a further example, the particular geometric shape can be a polyhedral nanoparticle having a plurality of faces, where at least three of the plurality of faces have a different shape or size as compared to a remainder of the plurality of faces. Additionally and/or alternatively, the mixture including the plurality of plasmonic photothermal nanoparticles can include different types of polyhedral shapes. For instance, the mixture can include a relative ratio of a first type of plasmonic photothermal nanoparticle and a second type of plasmonic photothermal nanoparticle to target a particular peak resonance wavelength.

The excitation of the photothermal nanoparticles takes place by means of an alternating field such as by an alternating electromagnetic and/or optical field. The excitation of the photothermal nanoparticles occurs in the range of ultraviolet light around 300 nm, visible light (e.g., in a range of 400 nm to 700 nm) to the infrared range 710 nm to 1000 nm and radio waves more than 1000 nm. Preferably, excitation of the photothermal nanoparticles occurs in the range of about 300 nm to 1500 nm. The wavelength of light at which peak excitation is achieved is dependent upon the geometry of the photothermal nanoparticles used in the reaction mixture/volume. For instance, the photothermal nanoparticles can be tuned/derived to have a variety of peak wavelengths ranging from about 300 nm to 1500 nm. In various embodiments, the photothermal nanoparticles can also be tuned/derived to have a variety of peak wavelengths by adjusting the geometry of the particle shape. For instance, the nanoparticles can be non-spherical and/or non-rod shaped. Such non-spherical and/or non-rod shaped nanoparticles have the following geometries as described in the non-limiting examples of: nanostar, nanotriangle/prism, nanocube, hexagonal, triangular and spherical nanoring, nanocage, nanosquare plate, trisoctahedra, rhombicadodecadra, truncated ditetragonal prism, tetrahexahedra, octahedra, decahedra, icosahedra, nanobar, and rice-like shapes.

In various embodiments, the reaction mixture/volume can include plasmonic, photothermal nanoparticles having a single geometric shape. Additionally and/or alternatively, the reaction mixture/volume can include a combination of nanoparticle geometries. As an illustration, a reaction mixture/volume can comprise nanoparticles having a nanostar geometry, and/or a reaction mixture can comprise nanoparticles having a nanostar geometry and nanoparticles having an octahedral geometry (as non-limiting examples). The particular geometry of the nanoparticles, as well as the combination of the nanoparticles, can be selected to achieve a particular peak absorption wavelength. For instance, a particular combination of nanoparticle geometries can be selected (e.g., used for the PCR) in order to achieve a particular peak wavelength such as in the range from about 300 nm to 1500 nm.

In various example embodiments, the nanoparticles are excited by a laser. More preferably, the laser light has a frequency that excites the surface plasmon resonance of the nanoparticles. The laser can supply the light continuously or as pulsed light. As non-limiting examples, the laser can be a gas laser, a diode laser, or a diode-pumped solid-state laser, among other types of lasers. The nanoparticles and/or the PCR mixture can be irradiated for around ten seconds, or otherwise a sufficient time for increasing the temperature from 45 degrees C. to 95 degrees C. In various embodiments, the energy of the radiation source (e.g., laser) is transferred to the photothermal nanoparticles due to the absorption of electromagnetic waves by the photothermal nanoparticles. The radiation source, which is used for the excitation of the nanoparticles, can also originate from sources such as a LED, a thermic radiator, a flash bulb, and/or by ultrasound.

Through the excitation of the nanoparticles, thermal energy is transferred from the excited nanoparticles to the surrounding reaction mixture/volume such that the temperature of the reaction mixture/volume is sufficient to denature the double-stranded nucleic acids in the reaction mixture/volume. In such embodiments, rapid PCR cycling times can be produced quickly (e.g., at up to 75 degrees C./second) through the excitation of the nanoparticles to carry out denaturation. Additionally, the annealing and elongation temperatures can also be more rapidly achieved through the excitation of the nanoparticles because only a small amount of energy has to be transferred to excite the nanoparticles. The excitation of the nanoparticles then heats the reaction volume (e.g., whole reaction volume, half reaction volume, less than half reaction volume, a small amount of reaction volume, etc.). For instance, by exciting the nanoparticles to heat the reaction mixture/volume, and using particular geometric shapes of nanoparticles, the PCR reaction mixture/volume can be heated at up to 75 degrees C./second to complete 30 or more cycles in less than 15 minutes.

Various geometric shapes of photothermal nanoparticles may be used to heat the reaction mixture/volume. The particular geometric shapes of the nanoparticles, as well as the chemical composition of the same, provide photothermal nanoparticles that are stable under light irradiation and have high photo-to-thermal conversion efficiency. The geometry of the photothermal nanoparticles are non-spherical and/or non-rod shaped. For example, the geometry of the photothermal nanoparticles can be selected from among the following shapes: nanostar, nanotriangle/prism, nanocube, nanoring, nanocage, nanosquare plate, trisoctahedra, rhombicadodecadra, truncated ditetragonal prism, tetrahexahedra, octahedra, decahedra, icosahedra, nanobar, and rice-like shapes.

The shapes of the nanoparticles can be defined in groups and/or categories. One group includes or refers to shapes having single component polyhedral nanoparticles and the other group includes or refers to shapes having multi-component (hybrid) polyhedral nanoparticles. The single component polyhedral nanoparticles group includes sub-groups or sub-categories such as polyhedral shapes/nanoparticles (e.g., cubes, prisms, octahedrons, and/or platonic shapes) and polyhedron frames/hollow polyhedrons (e.g., rings, cubic cages, and hollow structures). The multi-component group includes sub-groups or sub-categories such as alloys, core-shell shapes, and multi-shell shapes.

In various non-limiting example embodiments, the nanoparticles described are composed of noble metals. The nanoparticles can also be composed of metals with an inorganic surface coating. Additionally and/or alternatively, the nanoparticles can be composed of alloys, core-shells, and multi-shells. Examples of such metals and/or alloys include, but are not limited to, gold (Au), silver (Ag), platinum (Pt), palladium (Pd), iron (Fe), copper (Cu), aluminum (Al), zinc (Zn), and/or combinations thereof.

Alloys can be coated with an organic or inorganic surface coating. For example, the nanoparticles can be coated with an organic and/or inorganic surface coating to prevent interference of PCR-based reactions due to a bare particle surface and/or to enhance the stability of the nanoparticle under irradiation and during storage. Non-limiting examples of coating materials include: silica, silicon, synthetic polymers (such as PVP, thiol-terminated Polystyrene, polyacrylamide, etc.), oligo or polyethylene glycol, peptides, polysaccharides, etc. Examples are not so limited, and in various embodiments, the coating includes non-polymeric materials.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element. Also, although aspects and features may in some cases be described in individual figures, it will be appreciated that features from one figure or embodiment can be combined with features of another figure or embodiment even though the combination is not explicitly shown or explicitly described as a combination.

In the invention disclosed herein, plasmonic photothermal nanoparticles of a variety of different shapes and/or different shape combinations are designed and prepared for use as a heating media for PCR-based reaction mixtures. These nanoparticles absorb energy from a light source such as lasers or LEDs with wavelength reactions from about 300 nm to about 1500 nm and convert it to heat to heat up a PCR mixture rapidly, at up to 75 degrees C./second. These nanoparticles are also stable under light irradiation and have high photo-to-thermal conversion efficiency. The photothermal nanoparticles described herein can be composed of metals or alloys with or without inorganic or organic surface coatings. The shape and/or geometry of the photothermal nanoparticles impacts photo-to-thermal conversion efficiency and stability under laser irradiation or during storage as well as to determine peak wavelength. In the invention herein, the photothermal nanoparticles may be composed of metals including, but not limited to, gold (Au), silver (Ag), platinum (Pt), palladium (Pd), iron (Fe), copper (Cu), aluminum (Al), zinc (Zn), and combinations thereof. In specific examples, the nanoparticles are made essentially of gold or a gold-silver alloy. The geometry of the photothermal nanoparticles described herein are non-spherical and/or non-rod shaped including, but not limited to, nanostar, nanotriangle/prism, nanocube, nanoring, nanocage, nanosquare plate, trisoctahedra, rhombicadodecadra, truncated ditetragonal prism, tetrahexahedra, octahedra, decahedra, icosahedra, nanobar, rice-like shapes, and combinations thereof. With these geometries, the absorption peak wavelength of the nanoparticles can be tuned from about 300 nm up to about 1500 nm. The photothermal nanoparticles described in the present invention may also be coated with an organic or inorganic material(s) to prevent interference by PCR-based reaction components due to a bare particle surface and/or enhancement of the stability of the nanoparticle under irradiation and during storage. These coating materials include, but are not limit to, silica, silicon, synthetic polymers (such as PVP, thiol-terminated Polystyrene, polyacrylamide, etc.), oligo or polyethylene glycol, peptides, polysaccharides, and/or non-polymeric coatings, among others. To engage the photothermal property of the nanoparticles, the light source can be a laser or LED with the requirement being that the input power should be enough for rapid heating ramp at up to 75 degrees C./s. According to various example embodiments, the photothermal nanoparticles have a very different geometry including shapes that allow for modifying the nanoparticle's peak wavelength from about 300 nm to 1500 nm to enable application in quantitative PCR (qPCR). The described geometries, shapes, and/or surface coatings of the photothermal nanoparticles can provide higher photo-to-thermal conversion efficiency as well as higher shape stability during irradiation, thereby preventing nanoparticle melting during irradiation by the light source.

FIGS. 1A and 1B illustrate a diagram of a photothermal testing system to evaluate the nanoparticles photo-to-heat conversion for rapid nucleic acid amplification, in accordance with the present disclosure. As illustrated in FIGS. 1A and 1B, the system includes a light source 101, a PCR tube 103, a thermocouple 105, and a fan 109. The system includes a PCR tube 103 for receiving the reaction mixture comprising the photothermal nanoparticles. The PCR tube 103 can include a container, a chamber, an assembly, or other structure adapted to receive the reaction mixture and nanoparticles and provide optical access thereto. As illustrated in FIG. 1A, a thermocouple 105 can be used to measure the temperature change in the PCR tube 103 containing the photothermal nanoparticles.

The system further includes a light source 101 for irradiating the photothermal nanoparticles using an activation light beam such that the photothermal nanoparticles release heat sufficient to heat the surrounding reaction mixture. In various embodiments, the light source 101 can be embodied by a laser or LED (light-emitting diode) generating light at a wavelength coordinated with the plasmonic properties of the nanoparticles. As an illustration, the light source 101 can be a laser having the following specifications: an output wavelength of 808 nanometers (nm); output power of 2 watts (W); a divergence angle of 0.1 milliradian (mrad) to around 10 mrad adjustable; a rectangular laser shape; an exit pupil diameter of 5 millimeters (mm); an infrared optical aspheric glass lens optical system; a>Φ2 mm adjustable spot description; a working voltage of 3 volts (V) direct current; an operating current of 1.1 amps (A); a working temperature from −10 degrees C. to around 50 degrees C.; a storage temperature of −40 degrees C. to around 80 degrees C.; and a laser module dimension of Φ25 mm×40 mm and a circuit board dimension of Φ60 mm×40 mm×24 mm. The light source 101 can be part of a light generating assembly allowing a control of optical parameters of the activation light beam such as the wavelength, optical power, and duty cycle in embodiments where the light beam is pulsed, spot size, etc.

In various examples, the photothermal nanoparticle is characterized by photothermal properties sufficient for increasing a temperature of a mixture in contact with the photothermal nanoparticle. For instance, the photothermal nanoparticle may be characterized by photothermal properties sufficient for increasing a temperature of the mixture from 55 degrees C. to 95 degrees C. within 1 second. Additionally, the photothermal nanoparticle may be characterized by photothermal properties sufficient for increasing a temperature of the mixture from 55 degrees C. to 95 degrees C. within 2 seconds. Moreover, the photothermal nanoparticle may be characterized by photothermal properties sufficient for increasing a temperature of the mixture from 55 degrees C. to 95 degrees C. within 4 seconds.

As a further illustration, the photothermal nanoparticle may be characterized by photothermal properties sufficient for increasing a temperature of a mixture in contact with the photothermal nanoparticle at a rate of up to 75 degrees C. per second, at a rate of up to 40 degrees C. per second, at a rate of up to 20 degrees C. per second, and/or at a rate of up to 10 degrees C. per second. As used herein, photothermal properties refer to or include a shape, size, composition, and/or shell structure of the photothermal nanoparticle. For instance, as discussed with regards to FIGS. 2A-2U, various shapes, compositions, and/or shelled structures of photothermal nanoparticles may be used to select a particular heating rate for nucleic acid amplification.

By way of example, in the illustrated embodiment, the light source 101 generates an activation light beam having a wavelength of 808 nm resonant with the resonance of the photothermal nanoparticles in the PCR tube 103. As illustrated in FIG. 1B, the system can include a fan 109 disposed in proximity to the PCR tube 103 (e.g., the fan 109 may be disposed 1 cm away from the PCR tube 103 and the PCR tube 103 can be placed 5 cm away from the light source 101, as illustrated in FIG. 1A) and can be activated to accelerate the cooling of the reaction mixture during the cooling phases of the thermocycling. A fan controller preferably allows a control of the activation of the fan 109. Optionally, a timer can time the cycles between the PCR reactions.

Figure 2B:
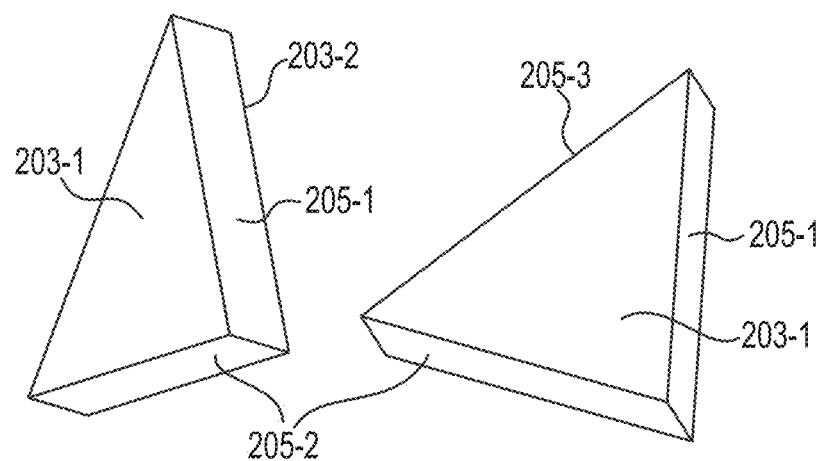
Figure 2C:
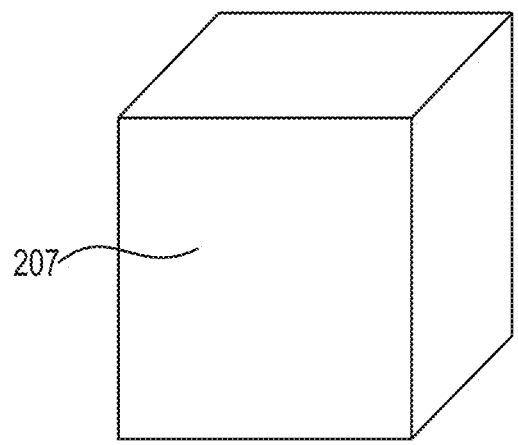
Figure 2D:
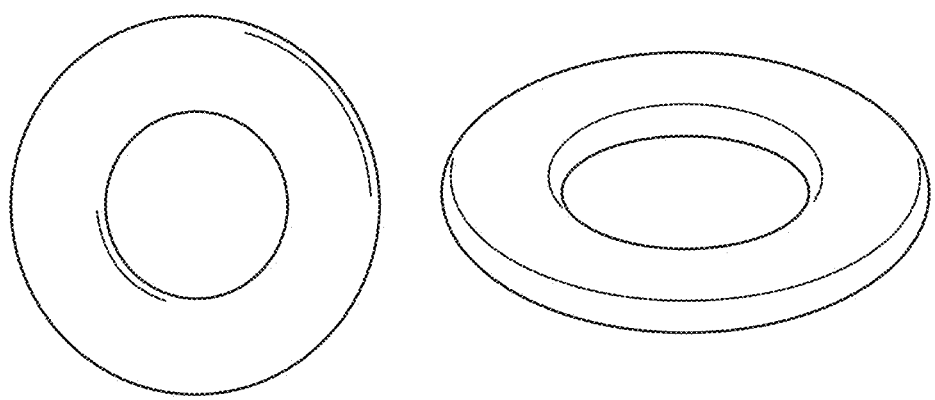
Figure 2E:
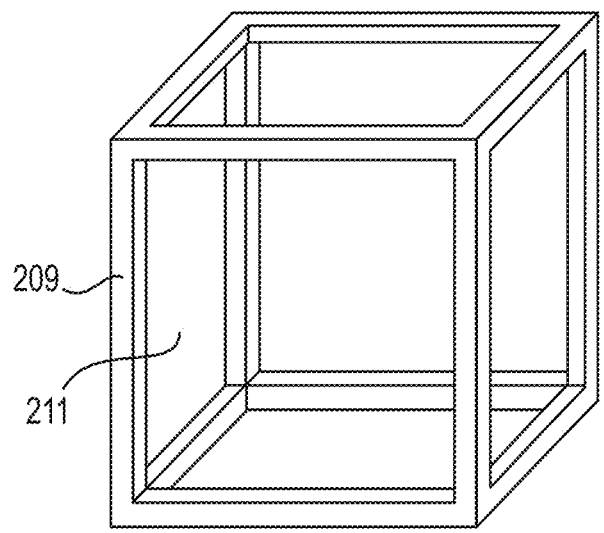
Figure 2F:
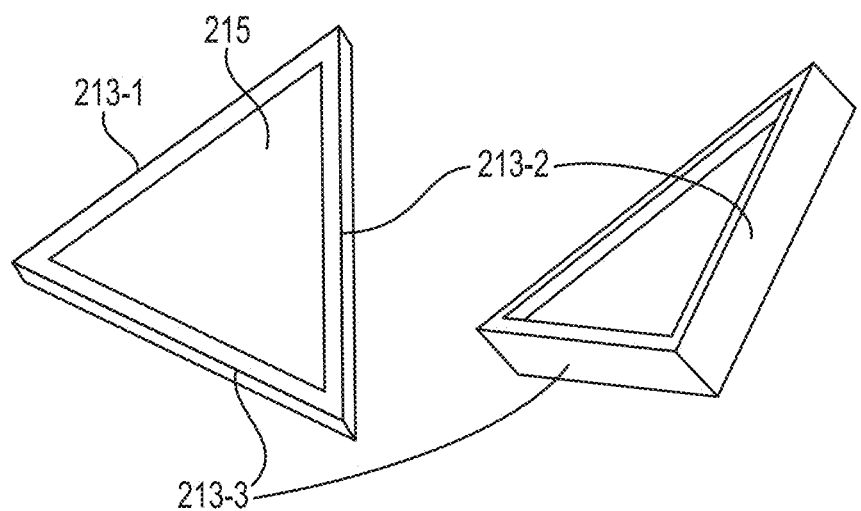
Figure 2G:
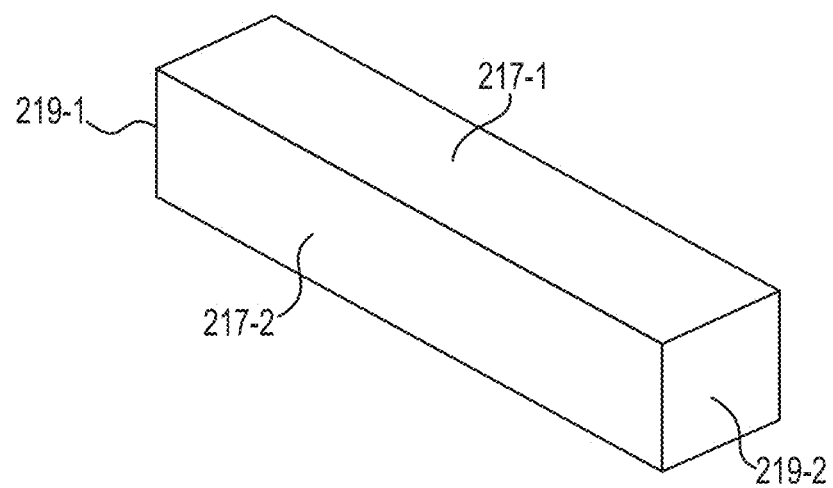
Figure 2H:
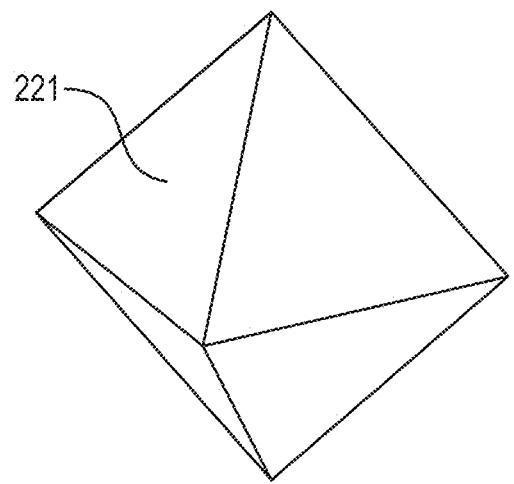
Figure 2I:
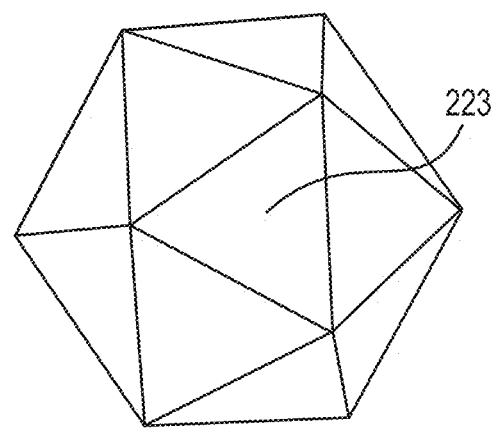
Figure 2J:
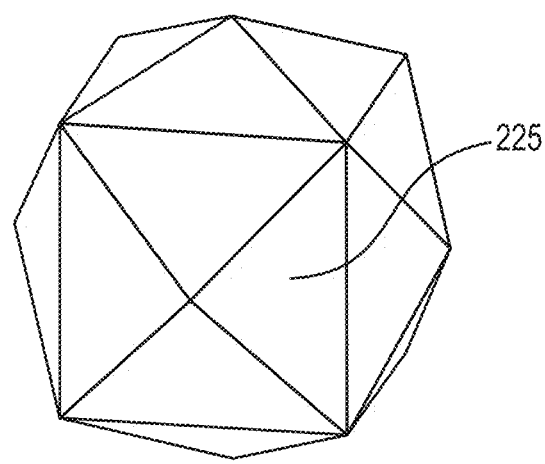
Figure 2K:
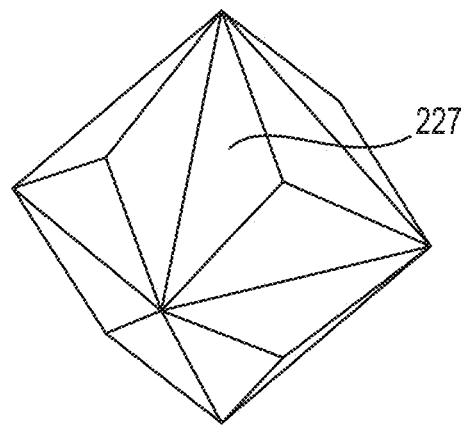
Figure 2L:
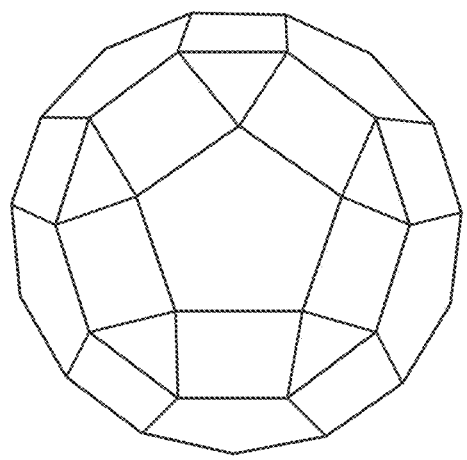
Figure 2M:
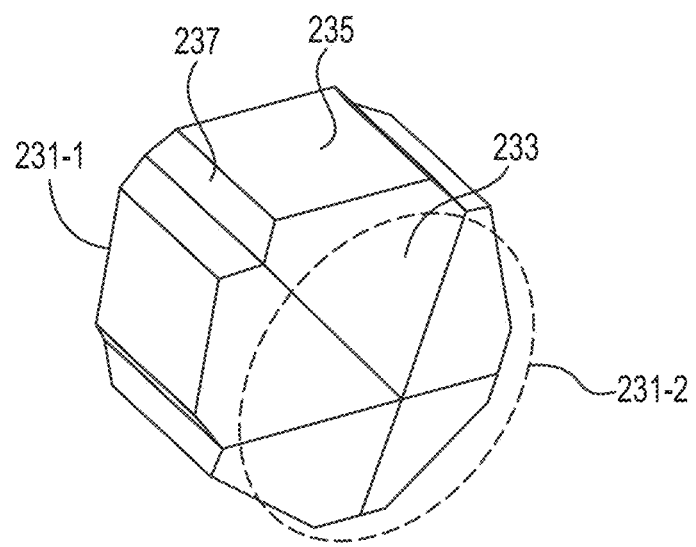
Figure 2N:
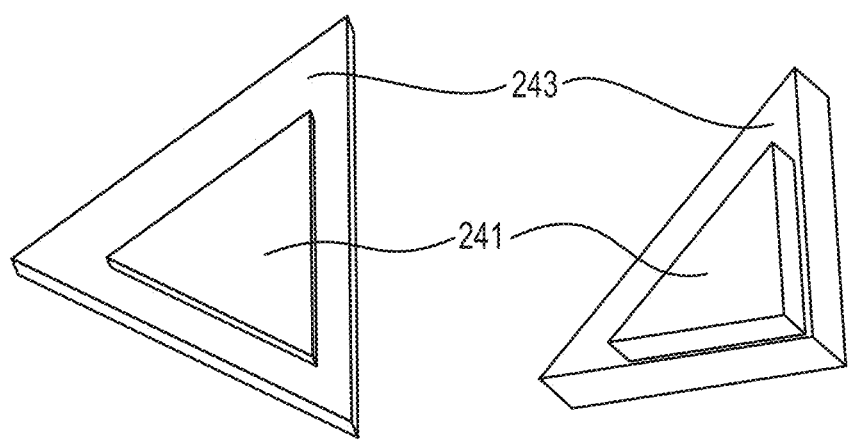
Figure 2O:
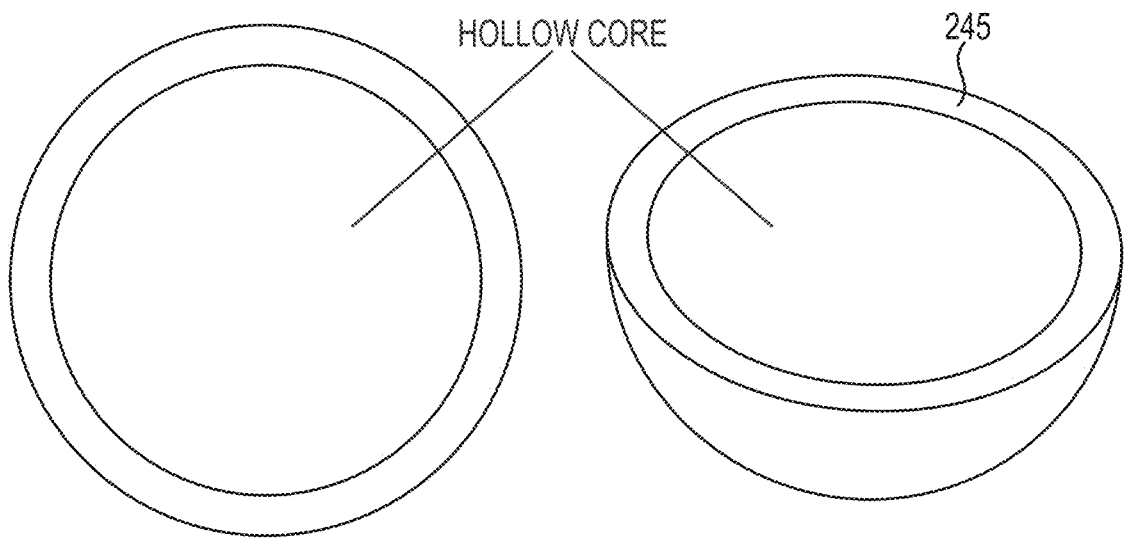
Figure 2P:
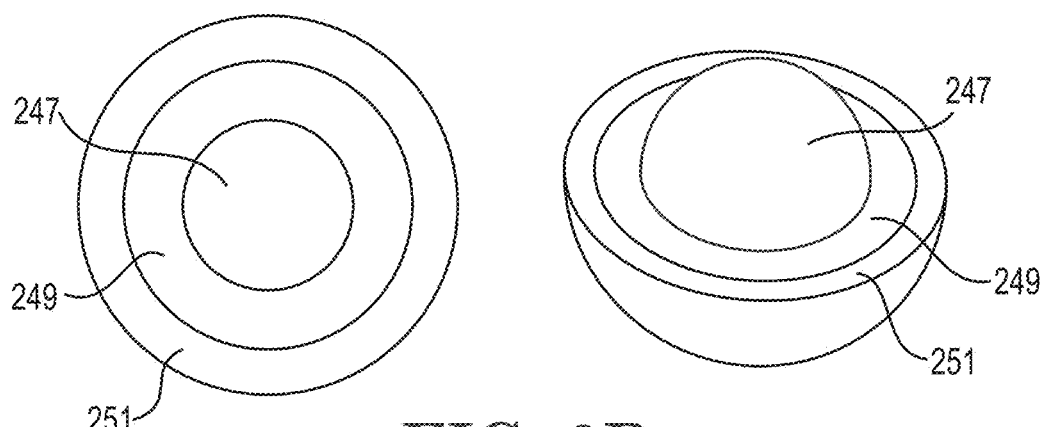
Figure 2Q:
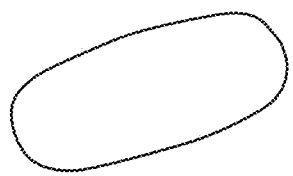
Figure 2R:
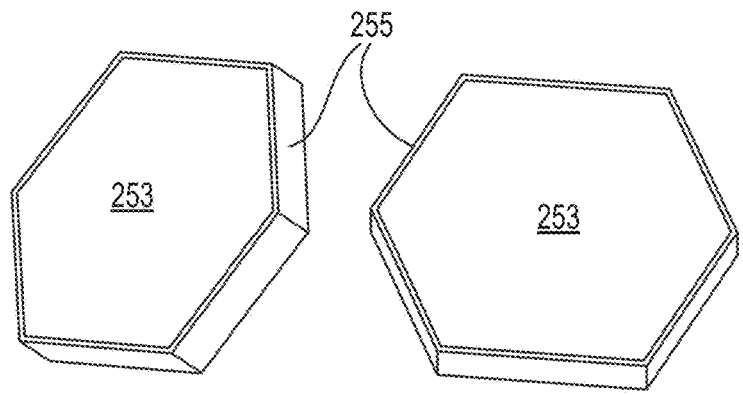
Figures 2S, 2T, 2U:
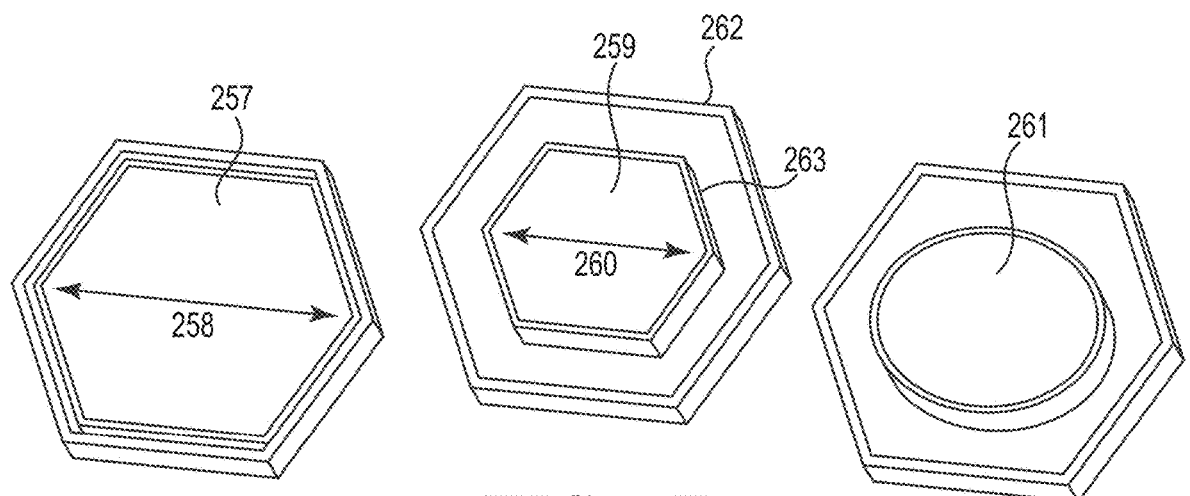

FIGS. 2A-2U illustrate example nanoparticles, in accordance with the present disclosure. As previously described, the nanoparticles can be a variety of geometric shapes. The particular geometric shapes of the nanoparticles, as well as the chemical composition of the same, provide photothermal nanoparticles that are stable under light irradiation and have high photo-to-thermal conversion efficiency.

The geometry of the photothermal nanoparticles are non-spherical and/or non-rod shaped. For example, the nanoparticles can include shapes having four or more faces and sphere-like shapes. In specific embodiments, the nanoparticles have four or more faces and can be polyhedral shaped. The faces can be polygonal faces that are planar, convex and/or concave (e.g., diagonal faces). The sphere-like shapes can include less than four faces that are curved, such as a sphere, a torus or ring, and spheroids. As further described below, the nanoparticles can be hollow, solid, or cored-shelled shaped.

The geometry of the photothermal nanoparticles can be generally categorized in groups. For example, the nanoparticles can be single component polyhedral nanoparticles. A single component polyhedral nanoparticle refers to or includes a nanoparticle comprised of a single material, such as platinum for example. A sub-group or sub-category of the single component polyhedral nanoparticle includes or refers to the shapes of the nanoparticles. For instance, the single component polyhedral nanoparticle can include polyhedral shapes such as cubes, prisms, octahedrons, and/or platonic shapes. Additionally and/or alternatively, the single component polyhedral nanoparticles can include polyhedral shapes, which are hollow, such that the nanoparticles are frames or cage-like. Examples of such polyhedral frames or hollow polyhedrons include cubic cages, regular rings, hexagonal rings, triangular rings, among other hollow structures.

In various embodiments, the polyhedral nanoparticles can have multiple components (e.g., a multi-component nanoparticle). For instance, the nanoparticles can be comprised of a combination of metallic elements (e.g., an alloy) and/or can have a number of layers/shells. The nanoparticles can have a single shell surrounding a core metal (e.g., a core-shell nanoparticle) and/or can have a plurality of shell layers surrounding a core metal (e.g., multi-shell nanoparticle). As such, the photothermal nanoparticle may be a multi-component polyhedral nanoparticle including a plasmonic core and more than one shell layer.

Each of the photothermal nanoparticles illustrated in FIGS. 2A-2U is characterized by photothermal properties sufficient for increasing a temperature of a mixture in contact with the photothermal nanoparticle. For instance, the photothermal nanoparticles may be characterized by photothermal properties sufficient for increasing a temperature of the mixture from 55 degrees C. to 95 degrees C. within 1 second, for increasing the temperature of the mixture from 55 degrees C. to 95 degrees C. within 2 seconds, and/or for increasing the temperature of the mixture from 55 degrees C. to 95 degrees C. within 4 seconds. Moreover, the photothermal nanoparticles may be characterized by photothermal properties sufficient for increasing the temperature of a mixture in contact with the photothermal nanoparticle at a rate of up to 75 degrees C. per second, at a rate of up to 40 degrees C. per second, at a rate of up to 20 degrees C. per second, and/or at a rate of up to 10 degrees C. per second.

More specifically, FIG. 2A illustrates an example nanostar-shaped nanoparticle. The nanostar shape includes or refers to a three-dimensional star polygon shape, such as regular star polyhedra, having self-intersecting faces and/or self-intersecting edges. As shown, the nanostar shape can be a regular star polyhedra, such as a Kepler-Poinsot polyhedra, including faces that are pentagrams, triangles, or pentagons. For instance, the nanostar-shaped nanoparticle illustrated in FIG. 2A includes self-intersecting triangular faces 201. Examples are not so limited, and example nanostar shapes include a small stellated dodecahedron, a great stellated dodecahedron, a great icosahedron, and a great dodecahedron. Other example nanostar shapes include polyhedra such as a pentagrammic prism, a pentagrammic dipyramid, a great didecicosahedron, and a great dodecicosacron. The uniform star polyhedra have regular faces or regular star polygon faces. The dual uniform star polyhedra have regular faces or regular star polygon vertex figures. Other example star shapes include the stellations of convex polyhedra and their duals, the faceting of the dual polyhedra, star polytopes, and star-domain star polyhedra. Additionally and/or alternatively, the nanoparticles may have a nanohexapod shape. As used herein, a nanohexapod nanoparticle refers to or includes a nanoparticle having an octahedral core and six arms grown on its vertices. Nanoparticles with a nanohexapod shape are also referred to herein as nanoparticles with a nanohexapod geometry.

FIG. 2B illustrates example triangular prism or triangular plate-shaped nanoparticles. The triangular plate-shaped or triangular prism shape includes or refers to a polyhedron having two triangular faces 203-1, 203-2 or bases, and three faces 205-1, 205-2, 205-3 joining corresponding sides of the triangular faces (e.g., rectangular faces). Other embodiments can include a triangular pyramid or a tetrahedron which includes or refers to a polyhedron having four triangular faces, six straight edges, and four vertex corners.

FIG. 2C illustrates an example nanocube-shaped nanoparticle. A nanocube shape includes or refers to a polyhedron having six square faces 207 with three of the faces meeting at each vertex. As shown, the nanocube can have six faces, twelve edges, and eight vertices. While not illustrated in FIG. 2C, the nanocube-shaped nanoparticle may be a concave nanocube such that each of the six square faces 207 has a concave surface.

FIG. 2D illustrates example ring-shaped nanoparticles. The ring shape includes a torus, e.g., a surface of revolution generated by circle or oval in three-dimensional shape above an axis coplanar with the circle or oval.

FIG. 2E illustrates an example nanocage-shaped nanoparticle. A nanocage-shaped nanoparticle is also referred to herein as a nanoparticle with a nanocage geometry. The nanocage shape is similar to the nanocube, with the cube being hollow (e.g., no faces). A nanocage shape includes or refers to a polyhedron having six square faces defined by edges. As shown, the nanocage can have twelve edges and eight vertices, which define the "faces" that are, in such embodiments, apertures. For instance, each "face" includes a square-shaped perimeter 209 which defines the boundaries of a hollow, square-shaped opening 211, on each face.

FIG. 2F illustrates example triangular ring-shaped nanoparticles. The triangular ring shape is similar to the triangular prism or triangular plate-shaped nanoparticles with the prism being hollow. For example, the triangular ring shape includes or refers to a polyhedron having three physical faces 213-1, 213-2, 213-3 (e.g., the illustrated rectangular faces) that join corresponding sides forming a triangular shape. The triangular shape formed by the intersecting faces 213-1, 213-2, and 213-3 define the boundaries of a hollow, triangular-shaped opening 215.

FIG. 2G illustrates an example nanobar-shaped nanoparticle. A nanobar shape includes or refers to a polyhedron having six faces with three of the faces meeting at each vertex. At least two of the rectangular faces can be squares, while a remainder of the faces can be rectangular, although embodiments are not so limited. For instance, as illustrated in FIG. 2G, faces 217-1 and 217-2 are rectangular, whereas faces 219-1 and 219-2 are square.

FIG. 2H illustrates an example octahedron-shaped nanoparticle. An octahedron includes or refers to a polyhedron having eight faces, twelves edges, and six vertices. In specific aspects, the eight faces 221 can be triangles with four of each of the faces meeting at each vertex. Although FIG. 2H illustrates a nanoparticle having bipyramid-shaped geometry, examples are not so limited. As illustrated, the nanoparticles described herein may have a non-bipyramid shaped geometry.

FIG. 2I illustrates an example icosahedron-shaped nanoparticle. An icosahedron shape includes or refers to a polyhedron having twenty faces, twelve vertices, and thirty edges. As shown, each of the twenty faces 223 can be triangular-shaped.

FIG. 2J illustrates an example tetrahexahedron-shaped nanoparticle. A tetrahexahedron shape includes or refers to a polyhedron having twenty-four faces 225 that are each triangular shaped, and four of each of the twenty-four faces correspond to a face of a cube.

FIG. 2K illustrates an example trisoctahedron-shaped nanoparticle. A trisoctahedron shape includes or refers to a polyhedron having twenty-four faces 227 that are each triangular shaped, and three of each corresponding to a face of an octahedron.

FIG. 2L illustrates an example rhombicosidodecahedron-shaped nanoparticle. A rhombicosidodecahedron shape includes or refers to a polyhedron having twenty triangular-shaped faces, thirty square shaped faces, twelve regular pentagonal faces, sixty vertices, and one-hundred twenty edges.

FIG. 2M illustrates an example decahedron-shaped nanoparticle. A decahedron includes or refers to a polyhedron with ten faces. In various embodiments, the decahedron can be an octagonal prism, a square antiprism, a square cupola, a pentagonal bipyramid, an augmented pentagonal prims, a pentagonal trapezohedron, or an enneagonal pyramid, among others. In various examples, the faces of the decahedron can include different geometric shapes. For instance, each of faces 231-1 and 231-2 (e.g., the top and bottom faces) can include a plurality of triangular faces 233, whereas each of the side faces can include a square or rectangular face 235 and a rectangular face 237 on opposing sides of the rectangular face 235.

A variety of the above-described shaped nanoparticles can be solid, hollow, core-shelled, or multi-shelled particles. A core-shelled particle includes or refers to a particle that is a composite structure having more than one concentric layer. A multi-core shell particle includes or refers to a core-shell particle with more than two concentric layers. Such particles can be formed by coating a nanoparticle with another kind of nanomaterial.

FIG. 2N illustrates example core-shell nanoprism-shaped nanoparticles. The core-shell nanoprism includes two nanoprisms, as described above, with one of the nanoprisms 241 being the interior, and the other 243 being formed around the interior nanoprism 241.

FIG. 2O illustrates example hollow nanosphere shaped nanoparticles. Nanosphere shaped nanoparticles are also referred to herein as nanoparticles with a nanospherical geometry. A hollow nanosphere shape includes or refers to a sphere 245 that has a hollow interior (e.g., hollow core).

FIG. 2P illustrates example nanoparticles composed of one nanosphere core with multiple nanosphere shells. The nanospheres with one core and multiple shells refers to three or more nanospheres with a solid interior. The most inner nanosphere 247 is the core, the second nanosphere 249 is formed around the first nanosphere 247, and the third (or more) nanosphere 251 is formed as an outer layer around the second nanosphere 249.

FIG. 2Q illustrates an example rice-like-shaped nanoparticle. The rice-like shape includes or refers to a spheroid or a flattened sphere shape. As shown, the rice-like shapes can be elongated or prolate spheroids.

FIG. 2R illustrates an example hexagonal plate-shaped nanoparticle. The hexagonal plate shape includes or refers to a polyhedron having two hexagonal faces or bases (e.g., face 253 and an opposing hexagonal face that is not expressly illustrated or numbered in FIG. 2R), and six faces joining corresponding sides of the two hexagonal faces. The six faces joining the corresponding hexagonal faces can be rectangular faces 255, as illustrated.

FIGS. 2S-2U illustrate example hexagonal ring-shaped nanoparticles. The hexagonal ring-shaped nanoparticle includes or refers to a hexagonal plate-shaped nanoparticle that has a hollow center or cavity. For instance, the hexagonal nanoparticle illustrated in FIG. 2S includes a hollow center 257, the hexagonal nanoparticle illustrated in FIG. 2T includes a hollow center 259, the hexagonal nanoparticle illustrated in FIG. 2S includes a hollow center 261. The hollow center or cavity can have a hexagonal shape or other shapes. As an example, hollow center 257 of FIG. 2S is hexagonal shaped, whereas hollow center 261 of FIG. 2U is circular shaped. Additionally, the hollow center of each hexagonal nanoparticle can have a different diameter. For instance, hollow center 257 of FIG. 2S has a diameter 258 which is greater than diameter 260 of hollow center 259 illustrated in FIG. 2T. The portion of the hexagonal ring-shaped nanoparticles between the exterior of the hexagonal faces and the hollow center or cavity can be hollow or solid, in various examples. As a non-limiting example, referring to FIG. 2T, the portion of the hexagonal ring-shaped particle between exterior surface 262 and interior surface 263 can be hollow or solid.

A number of specific embodiments are directed to systems and/or kits that include a plurality of the one or more above-described photothermal nanoparticles, DNA polymerase, and reaction reagent. The DNA polymerase is thermostable. The reaction reagent includes dNTPs, buffer, Mg+ (e.g., Magnesium Chloride (MgCl2)), and, optionally, a stabilizing agent. The components of the kit can each be provided in separate volumes (e.g., containers) and/or can be combined into one or more volume/container/mixture. For example, the nanoparticles, DNA polymerase, and reaction agent can all be in one container. In other embodiments, the DNA polymerase and reaction reagents are combined into a master mix and contained in a first container and the nanoparticles are in a separate container.

In various embodiments, the plasmonic photothermal nanoparticles can be either suspended in the solution or secured to a microfluidic chip (microchip) or surface of a plate for housing a reaction mixture. As such, the PCR tube or PCR plate well can have nanoparticles as heating media described herein, PCR reaction mixture including nucleic acid template and polymerase enzyme for performance of PCR as described herein. As an illustration, the PCR reaction mixture may be formed with the heating media comprising the photothermal nanoparticles fabricated on the multi-well plate, where the photothermal nanoparticles have a nanorod geometry and are made essentially of gold.

The nucleic acid capable of being amplified using the present invention includes, but is not limited to, DNA (single-stranded, double-stranded, linear, covalently closed, supercoiled and relaxed circular forms) or RNA (single stranded, double stranded, linear or covalently closed), or a combination of DNA and RNA.

As used herein, the term "mixture" encompasses any biological material either naturally occurring or scientifically engineered, which contains at least one nucleic acid in addition to other non-nucleic acid material, such as biomolecules (e.g., proteins, polysaccharides, lipids, low molecular weight enzyme inhibitors, oligonucleotides, primers, templates), polyacrylamide, trace metals, organic solvents, etc. Examples of naturally-occurring mixtures include, but are not limited to, whole blood, blood plasma, and other body fluids as well as tissue cell cultures obtained from humans, plants, or animals. Examples of scientifically-engineered mixtures include, but are not limited to, lysates, nucleic acid samples eluted from agarose and/or polyacrylamide gels, solutions containing multiple species of nucleic acid molecules resulting either from nucleic acid amplification methods such as PCR amplification or reverse transcription polymerase chain reaction (RT-PCR) amplification or from RNA or DNA size selection procedures, and solutions resulting from post-sequencing reactions.

Terms to exemplify orientation, such as upper/lower, left/right, top/bottom, and above/below, may be used herein to refer to relative positions of elements as shown in the figures. It should be understood that the terminology is used for notational convenience only and that in actual use the disclosed structures may be oriented different from the orientation shown in the figures. Thus, the terms should not be construed in a limiting manner.

The skilled artisan would recognize that various terminology as used in the Specification (including claims) connote a plain meaning in the art unless otherwise indicated. The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "sample", as used herein, generally refers to any material containing nucleic acid, including for example foods and allied products, clinical, and environmental samples. However, the sample will generally be a biological sample, which may contain any viral or cellular material, including all prokaryotic or eukaryotic cells, viruses, bacteriophages, mycoplasmas, protoplasts, and organelles. Such biological material may thus comprise all types of mammalian and non-mammalian animal cells, plant cells, algae including blue-green algae, fungi, bacteria, protozoa, etc. Representative samples thus include whole blood and blood-derived products such as plasma, serum and buffy coat, urine, feces, cerebrospinal fluid or any other body fluids, tissues, cell cultures, cell suspensions, etc. The sample may comprise a lysate. The sample may also include relatively pure starting material such as a PCR product or semi-pure preparations obtained by other nucleic acid recovery processes.

Based upon the above discussion and illustrations, those skilled in the art will readily recognize that various modifications and changes may be made to the various embodiments without strictly following the exemplary embodiments and applications illustrated and described herein. For example, methods as exemplified in the Figures may involve steps carried out in various orders, with one or more aspects of the embodiments herein retained, or may involve fewer or more steps. Such modifications do not depart from the true spirit and scope of various aspects of the disclosure, including aspects set forth in the claims.

Experimental/More Detailed Embodiments

As further illustrated below in connection with the experimental embodiments, photothermal cycles for rapid PCR were conducted with photothermal nanoparticles having different shapes and similar absorbance as described herein. Particular examples include photothermal cycles using different photothermal nanoparticles: gold nanostars (e.g., gold nanostars coated with polyethylene glycol (PEG)) and silver nanoprisms (e.g., silver triangular nanoplates).

Figure 3A:
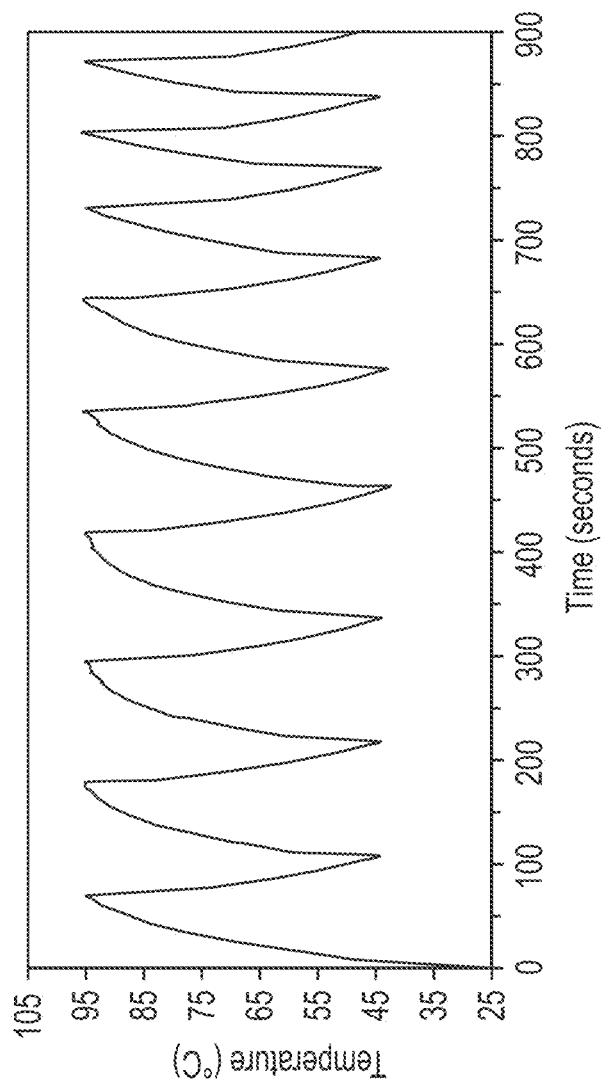
FIG. 3A illustrates example photothermal cycles of silver nanoprisms coated with polyvinylpyrrolidone in accordance with the present disclosure.
Figure 3B:
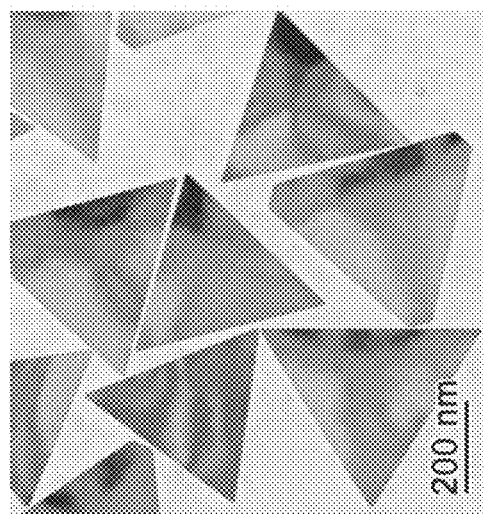
FIG. 3B illustrates an example transmission electron microscope (TEM) image of silver nanoprisms in accordance with the present disclosure.
Figure 3D:
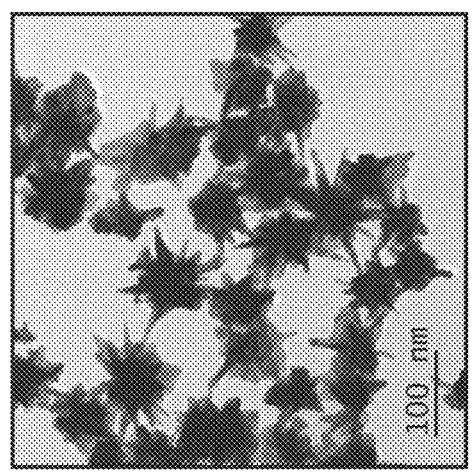
FIG. 3D illustrates an example TEM image of gold nanostars in accordance with the present disclosure.
Figure 3C:
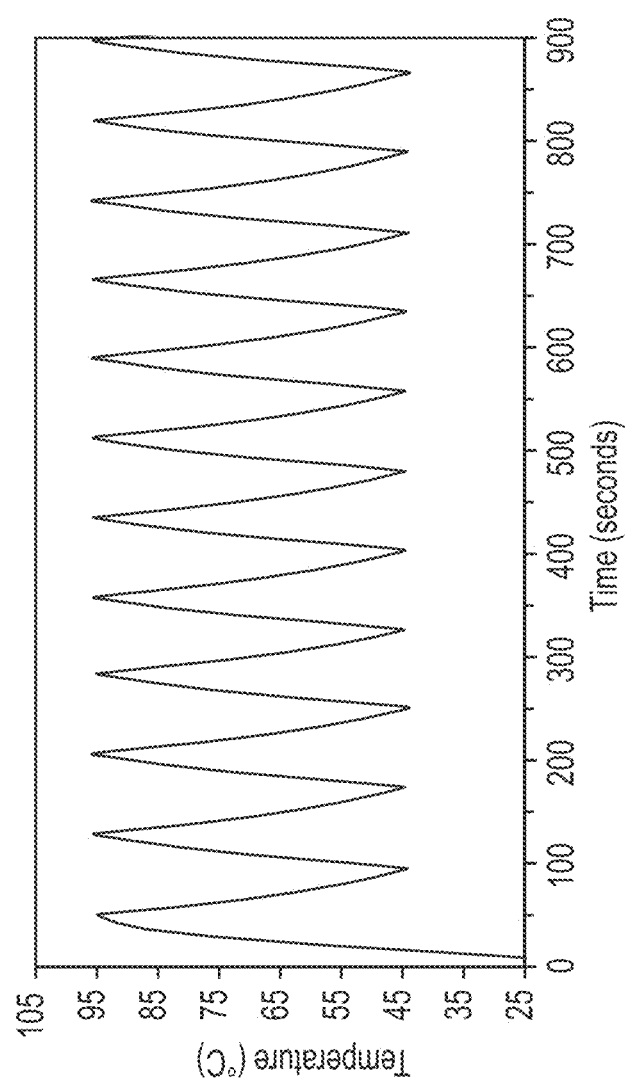
FIG. 3C illustrates example photothermal cycles of gold nanostars coated with polyethylene glycol in accordance with the present disclosure.

As a particular example, FIG. 3A illustrates photothermal cycles of silver nanoprisms coated with polyvinylpyrrolidone in accordance with the present disclosure. FIG. 3C illustrates photothermal cycles of gold nanostars coated with polyethylene glycol in accordance with the present disclosure. In each of the illustrated graphs, photothermal nanoparticles in GoTaq® G2 Hot Start PCR Mastermix solutions (2 optical density (O.D), 25 uL) were irradiated with 2 W/cm2 laser and photothermal cycles were recorded over 15 minutes, and then the respective solutions irradiated continuously to test the nanoparticle degradation at 95 degrees C. As illustrated in FIG. 3A, the silver nanoprisms demonstrated an average heating rate (from 45 degrees C. to 95 degrees C.) of 60.6 seconds, and an average cooling rate (from 95 degrees C. to 45 degrees C.) of 39.1 seconds. To achieve various heating rates, different concentrations of photothermal nanoparticles (0-50 O.D) with various laser powers or various volumes of PCR mastermix solutions (5-50 uL) can be used. FIG. 3B illustrates an example transmission electron microscope (TEM) image of silver nanoprisms in accordance with the present disclosure.

Similarly, FIG. 3C illustrates example photothermal cycles of gold nanostars coated with polyethylene glycol in accordance with the present disclosure. As illustrated, the gold nanostars coated with PEG demonstrated an average heating rate (from 45 degrees C. to 95 degrees C.) of 31.7 seconds, and an average cooling rate (from 95 degrees C. to 45 degrees C.) of 45.3 seconds. FIG. 3D illustrates an example TEM image of gold nanostars in accordance with the present disclosure.

Similarly, FIG. 3E illustrates example photothermal cycles of gold nanocages coated with polyethylene glycol in accordance with the present disclosure. As illustrated, the gold nanocages coated with PEG demonstrated an average heating rate (from 45 degrees C. to 95 degrees C.) of 2.5 seconds, and an average cooling rate (from 95 degrees C. to 45 degrees C.) of 17 seconds. To achieve various heating rates, different concentrations of photothermal nanoparticles (0-50 O.D), laser power, or various volumes of PCR mastermix solutions (5-50 uL) can be used. FIG. 3F illustrates an example TEM image of gold nanocages in accordance with the present disclosure.

Figure 3G:
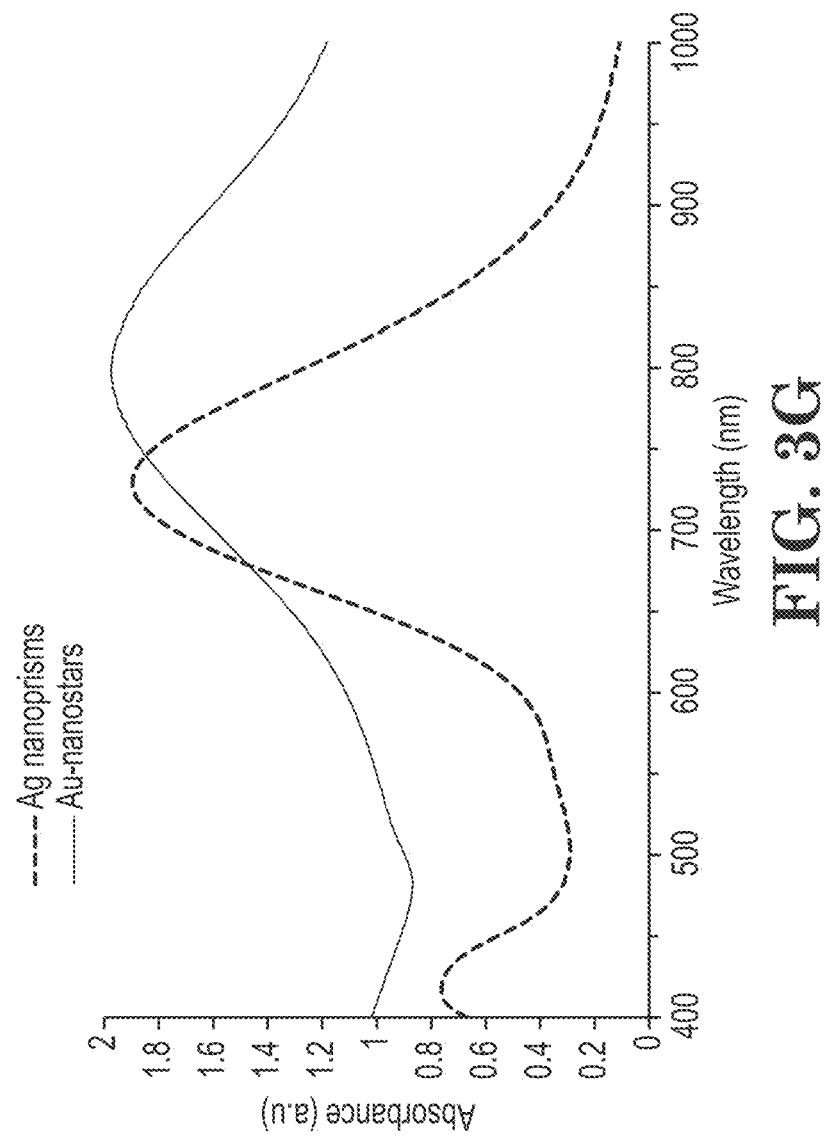
FIG. 3G illustrates an example ultraviolet-visible spectrum showing the maximum light absorbance peak of gold nanostars and silver nanoprisms in accordance with the present disclosure.

FIG. 3G illustrates an example ultraviolet-visible spectrum showing the maximum light absorbance peak of gold nanostars and silver nanoprisms in accordance with the present disclosure. As illustrated in FIG. 3G, the silver nanoprisms demonstrated absorbance intensity of 1.897 A.U.s at a peak wavelength of 726 nm. The gold nanostars demonstrated absorbance intensity of 1.975 A.U.s at a peak wavelength of 798 nm.

Figures 4A, 4B:
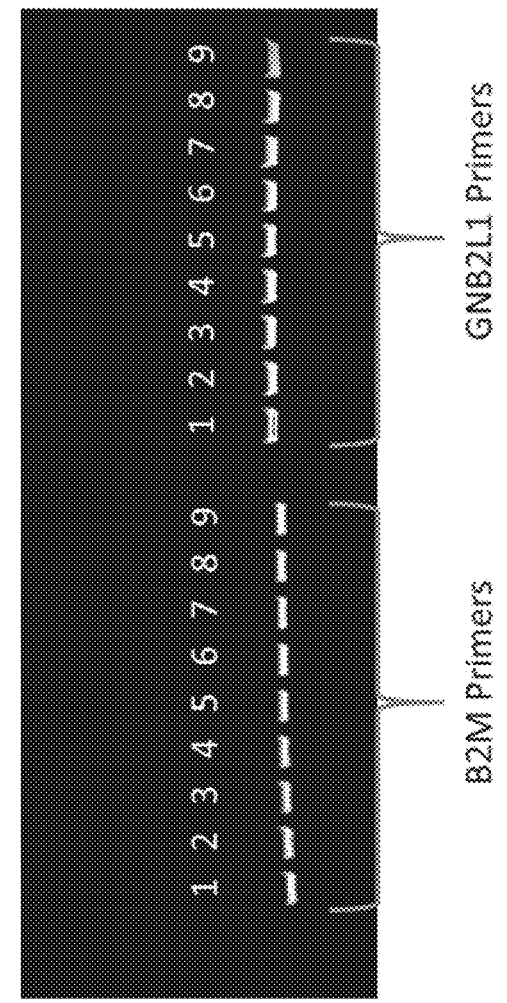
FIGS. 4A and 4B illustrate gel electrophoresis results from rapid nucleic acid amplification using photothermal gold nanocages in accordance with the present disclosure.

FIGS. 4A, and 4B illustrate gel electrophoresis results from rapid nucleic acid amplification inhibition using photothermal nanocages in accordance with the present disclosure. In the example illustrated in FIGS. 4A and 4B, PCR was performed using a cDNA template made with dT primer and RTX Exo+GoTaq® G2 Hot Start Mastermix. 200 nM of two different primers were used, beta 1 microglobulin (B2M) primers (on the left of FIG. 4B) and guanine nucleotide-binding protein subunit beta-2-like 1 (GNB2L1) primers (on the right of FIG. 4B). Gold nanocages coated with PEG were added to the reaction mixture in concentrations from 0 to 16 O.D. The total reaction mixture volume was 25 μL. The solution was heated for 2 minutes at 95 degrees C., and then cycled according to the following pattern 35 times: 30 seconds at 95 degrees C., 30 seconds at 60 degrees C., and 30 seconds at 72 degrees C. As illustrated in FIG. 4B, consistent results were achieved at each of the nanoparticle concentrations used during PCR indicating that there was no significant PCR inhibition observed as a result of adding the gold nanocages to the PCR reaction mixture.

Figure 5:
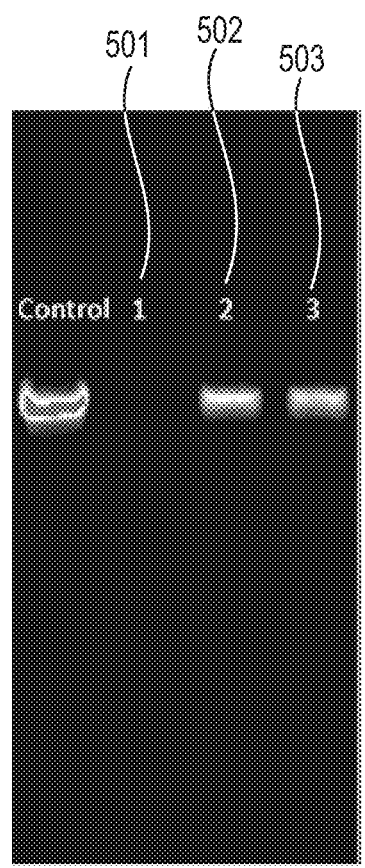
FIG. 5 illustrates gel electrophoresis results from rapid nucleic acid amplification using photothermal nanocages in accordance with the present disclosure.

FIG. 5 illustrates gel electrophoresis results from rapid nucleic acid amplification using photothermal nanocages in accordance with the present disclosure. In the example illustrated in FIG. 5, a reaction mixture consisting of non-hot start recombinant Taq DNA polymerase, a PCR nucleotide mixture (Deoxyadenosine triphosphate (dATP), Deoxycytidine triphosphate (dCTP), Deoxyguanosine triphosphate (dGTP) and Deoxythymidine triphosphate (dTTP)), a forward and reverse primer, a PCR buffer, 50 ng of human genomic DNA, and 2 O.D of PEGylated gold nanocages was prepared on ice. The PCR primers were designed to amplify a 337 base pair portion of the Human Beta-globin gene. 20 μl of the reaction mixture was added to a 0.2 ml PCR tube and overlaid with 15 μl of mineral oil and left on ice. A 2-step photonic PCR cycling was performed in a prototype instrument. 35 cycles were performed as follows: temperature 1 (T1) was set at approximately 94° C. and temperature 2 (T2) was set at approximately 64° C. Both temperatures were previously confirmed with a thermocouple probe placed in the reaction mix and cycling with the laser at 70%. To achieve T1, the laser was active/on and excited the nanoparticles and heated them, which in turn heats the reaction mix. The temperature was measured using an infrared (IR) sensor, and after the reaction mix reached the proper temperature, the laser was turned off, and a fan activated to cool the reaction mixture to the proper temperature that then activated the laser, thus initiating another cycle. Three different T1 reaction temperatures were tested in 3 separate reaction tubes corresponding to 94° C. (well 1), 90° C. (well 2), and 86° C. (well 3). The amplifications were done in less than 15 minutes. A control reaction was performed by placing a reaction tube in a traditional Peltier thermocycler and cycled for 35 cycles each consisting of a 2 second denaturation step at 95° C. and an annealing step of 6 seconds at 65° C. This reaction cycling was used as a positive confirmation of the ability of the reaction mix to produce an amplicon of the proper size in the presence of the nanoparticles. To confirm amplification, all 4 reactions were run on a 2% Agarose gel containing ethidium bromide and imaged using a UV camera system.

As demonstrated in FIG. 5, amplification product was seen clearly in well 2 and well 3 proving the effectiveness of the photothermal nanoparticle-mediated PCR reaction of the present invention. No product was seen in well 1, which could be attributed to the discrepancy between the temperature measured by IR sensor and the real temperature in solution.

What is claimed, without limitation:

1. A method for rapid amplification of a nucleic acid molecule with a polymerase chain reaction comprising:
   forming a reaction mixture including a nucleic acid template, a polymerase enzyme, and a heating media on a substrate, a microchip, a plate, or a multi-well plate including photothermal nanoparticles immobilized on a substrate surface of the substrate, fabricated on the microchip, or fabricated on a surface of the plate or a well of the multi-well plate, wherein the photothermal nanoparticles are made essentially of gold and have a particular geometric shape and comprise a single component or a multi-component, and the photothermal nanoparticles are further categorized by surface plasmon resonance with a resonance wavelength in a particular range to convert energy absorbed from a light source to sufficiently heat a volume of a composition for transcription of a new nucleic acid strand, and wherein the particular geometric shape is selected from the group consisting of: polyhedral, spheroid, torus, and hollow shapes; and
   irradiating the reaction mixture at a wavelength ranging from 300 nm to 1500 nm, depending on the particular geometric shape of the photothermal nanoparticles, sufficient for heating the reaction mixture at a rate up to 75 degrees Celsius per second to complete amplification thermal cycles in 15 minutes or less time by adjusting a concentration of photothermal nanoparticles.

2. The method of claim 1, comprising:
   immobilizing or fabricating the photothermal nanoparticles on the substrate surface, the microchip, or the surface of the plate or the well of the multi-well plate and then forming the reaction mixture including the nucleic acid template, the polymerase enzyme, and the heating media wherein the photothermal nanoparticles have a particular geometry comprising a nanostar or nanocage geometry.

3. The method of claim 1, comprising forming the reaction mixture with the heating media that includes the photothermal nanoparticles with a particular geometry and a particular chemical coating sufficient to maintain stability under irradiation and to maintain a high photo-to-thermal conversion efficiency.

4. The method of claim 1, comprising forming the reaction mixture with the heating media comprising the photothermal nanoparticles that include metals with an organic surface coating.

5. The method of claim 4, wherein the organic surface coating is selected from the group consisting of: synthetic polymers, oligo or polyethylene glycol, peptides, polystyrene and polysaccharides.

6. The method of claim 1, comprising forming the reaction mixture with the heating media comprising the photothermal nanoparticles that include alloys with an inorganic surface coating.

7. The method of claim 6, wherein the inorganic surface coating is selected from silica and silicon.

8. The method of claim 1, comprising forming the reaction mixture with the heating media comprising the photothermal nanoparticles that include metals selected from the group consisting of: gold (Au), silver (Ag), platinum (Pt), palladium (Pd), iron (Fe), copper (Cu), aluminum (Al), and zinc (Zn), core-shell, multi-shell, alloys, and combinations thereof.

9. The method of claim 1, comprising forming the reaction mixture with the heating media comprising the photothermal nanoparticles fabricated on the multi-well plate, wherein the photothermal nanoparticles have a nanocage geometry and are made essentially of gold.

10. The method of claim 1, comprising forming the reaction mixture with the heating media comprising the photothermal nanoparticles fabricated on the multi-well plate, wherein the photothermal nanoparticles have a nanostar geometry and are made essentially of gold.

11. The method of claim 1, wherein irradiating the reaction mixture comprises irradiating the reaction mixture sufficient for heating the reaction mixture at the rate that is at least 20 degrees Celsius per second and up to 75 degrees Celsius per second.

12. The method of claim 1, wherein irradiating the reaction mixture comprises irradiating the reaction mixture sufficient for heating the reaction mixture at the rate that is at least 20 degrees Celsius per second and up to 75 degrees Celsius per second to complete 30 or more amplification thermal cycles in the 15 minutes or less time by adjusting the concentration of photothermal nanoparticles.

13. The method of claim 1, wherein the photothermal nanoparticles are non-spherical and non-rod shape.

* * * * *